United States Patent
Thian et al.

(10) Patent No.: US 10,842,611 B2
(45) Date of Patent: Nov. 24, 2020

(54) TISSUE SCAFFOLD DEVICE AND METHOD FOR FABRICATING THEREOF

(71) Applicant: NATIONAL UNIVERSITY OF SINGAPORE, Singapore (SG)

(72) Inventors: Eng San Thian, Singapore (SG); Zuyong Wang, Singapore (SG); Ee Jen Wilson Wang, Singapore (SG); Minghui Hong, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 80 days.

(21) Appl. No.: 15/526,429

(22) PCT Filed: Nov. 3, 2015

(86) PCT No.: PCT/SG2015/050431
§ 371 (c)(1),
(2) Date: May 12, 2017

(87) PCT Pub. No.: WO2016/076791
PCT Pub. Date: May 19, 2016

(65) Prior Publication Data
US 2018/0296316 A1  Oct. 18, 2018

(30) Foreign Application Priority Data
Nov. 13, 2014 (SG) .......................... 10201407543V

(51) Int. Cl.
*A61F 2/08* (2006.01)
*A61L 27/12* (2006.01)
(Continued)

(52) U.S. Cl.
CPC .............. *A61F 2/08* (2013.01); *A61F 2/0077* (2013.01); *A61L 27/12* (2013.01); *A61L 27/18* (2013.01);
(Continued)

(58) Field of Classification Search
CPC ...... A61L 2430/10; A61L 27/12; A61L 27/18; A61L 27/24; A61L 27/56; A61F 2/08;
(Continued)

(56) References Cited

U.S. PATENT DOCUMENTS

| 7,824,701 B2 | 11/2010 | Binette | |
| 2005/0095695 A1* | 5/2005 | Shindler | B82Y 5/00 435/285.1 |

(Continued)

FOREIGN PATENT DOCUMENTS

| EP | 2210971 A1 | 7/2010 |
| WO | 98/14135 A1 | 4/1998 |

(Continued)

OTHER PUBLICATIONS

Ramakrishna, S., et al. "Electrospun Nanofibers; Solving Global Issues". Materials Today, Mar. 2006; vol. 9(3), p. 40-50.*
(Continued)

*Primary Examiner* — Brian A Dukert
*Assistant Examiner* — Rebecca Lynee Zimmerman
(74) *Attorney, Agent, or Firm* — Volpe Koenig

(57) ABSTRACT

According to various embodiments, there is provided a tissue scaffold device including a porous core including a plurality of fibres; and an outer portion at least substantially surrounding the porous core, the outer portion including a plurality of pores elongated along a longitudinal axis of the tissue scaffold device.

8 Claims, 17 Drawing Sheets

(51) Int. Cl.
  *A61L 27/18* (2006.01)
  *A61L 27/24* (2006.01)
  *A61L 27/56* (2006.01)
  *A61F 2/00* (2006.01)
  *D01D 5/00* (2006.01)

(52) U.S. Cl.
  CPC .............. *A61L 27/24* (2013.01); *A61L 27/56* (2013.01); *A61F 2002/0081* (2013.01); *A61F 2210/0004* (2013.01); *A61F 2230/0008* (2013.01); *A61F 2230/0069* (2013.01); *A61F 2230/0091* (2013.01); *A61F 2240/001* (2013.01); *A61F 2250/0023* (2013.01); *A61F 2250/0028* (2013.01); *A61L 2430/10* (2013.01); *D01D 5/0007* (2013.01); *D10B 2101/10* (2013.01)

(58) Field of Classification Search
  CPC ............ A61F 2/0077; A61F 2210/0004; A61F 2230/0069; A61F 2240/001; A61F 2230/0008; A61F 2250/0023; A61F 2230/0091; A61F 2002/0081; A61F 2250/0028; D10B 2101/10; D01D 5/0007
  USPC ............ 623/13.17, 13.2, 13.15, 13.11, 20.17
  See application file for complete search history.

(56) References Cited

U.S. PATENT DOCUMENTS

| | | | |
|---|---|---|---|
| 2008/0220042 A1* | 9/2008 | Hashi | A61K 38/58 514/1.1 |
| 2009/0018643 A1* | 1/2009 | Hashi | A61F 2/82 623/1.15 |
| 2009/0075382 A1 | 3/2009 | Sachlos | |
| 2011/0238179 A1 | 9/2011 | Laurencin | |
| 2013/0096679 A1 | 4/2013 | Laurencin | |
| 2013/0144400 A1 | 6/2013 | Day | |
| 2013/0172846 A1* | 7/2013 | Bellamkonda | A61K 9/0092 604/500 |
| 2013/0178949 A1* | 7/2013 | Bowlin | D01D 5/0061 623/23.72 |

FOREIGN PATENT DOCUMENTS

| | | |
|---|---|---|
| WO | 09/099570 A2 | 8/2009 |
| WO | 2014/047379 A1 | 3/2014 |

OTHER PUBLICATIONS

Woodruff, Maria A. and Hutmacher, Dietmar W. The return of a forgotten polymer; Polycaprolactone in the 21st Century. Progress in Polymer Science (2010).*

Park et al ("Hybrid Microfabrication of Nanofiber-Based Sheets and Rods for Tissue Engineering Applications". Journal of Laboratory Automation, Dec. 2013:18(6) p. 494-503.) (Year: 2013).*

Baker, B. M., et al. The potential to improve cell infiltration in composite fiber-aligned electrospun scaffolds by the selective removal of sacrificial fibers. Biomaterials. 2008, 29: 2348-2358.

Burdick, J.A., et al. Biomaterials for Tissue Engineering Applications: A Review of the Past and Future Trends, 2011 [Retrieved on Dec. 23, 2015] (DOI: 10.1007/978-3-7091-0385-2) p. 165.

Caliari, S. R. The development of collagen-GAG scaffold-membrane composites for tendon tissue engineering. Biomaterials. 2011, 32: 8990-8998.

Cooper, J. A., et al. Fiber-based tissue-engineered scaffold for ligament replacement: design considerations and in vitro evaluation. Biomaterials. 2005, 26: 1523-1532.

Gazielly, D. F., et al. Functional and anatomical results after rotator cuff repair. Clinical Orthopaedics and Related Research. 1994, 304: 43-53.

Gulotta, L.V. et al. Rodeo. Application of bone marrow-derived mesenchymal stem cells in a rotator cuff repair model. The American Journal of Sports Medicine. 2009, 37: 2126-2133.

Kew, S. J., et al. Regeneration and repair of tendon and ligament tissue using collagen fibre biomaterials. Acta Biomaterialia. 2011, 7: 3237-3247.

Ouyang, H.W., et al. Knitted poly-lactide-co-glycolide scaffold loaded with bone marrow stromal cells in repair and regeneration of rabbit Achilles tendon. Tissue Engineering. 2003, 9: 431-439.

Park, S-Het et al., Hybrid Microfabrication of Nanofiber-Based Sheets and Rods for Tissue Engineering Applications. Journal of Laboratory Automation, Dec. 2013, vol. 18, No. 6, pp. 494-503. [Retrieved on Dec. 18, 2015] (DOI:10.1177/221106821350096.

Teh, T.K., et al. Aligned fibrous scaffolds for enhanced mechanoresponse and tenogenesis of mesenchymal stem cells. Tissue engineering. Part A. 2013, 19: 1360-1372.

Zamani, F. et al., Promotion of spinal cord axon regeneration by 3D nanofibrous core-sheath scaffolds. Journal of Biomedical Materials Research Part A, Aug. 7, 2013, vol. 102, No. 2, pp. 506-513. [Retrieved on Dec. 18, 2015] (DOI:10.1002/JBM.A.34703).

Extended European Search Report issued in corresponding European Patent Appln. No. 15859055.4 dated Jun. 14, 2018, consisting of 8 pp.

* cited by examiner

TISSUE SCAFFOLD DEVICE AND METHOD FOR FABRICATING THEREOF

CROSS-REFERENCE TO RELATED APPLICATIONS

This application claims the benefit of Singapore Patent Application number 10201407543V filed 13 Nov. 2014, the entire contents of which are incorporated herein by reference for all purposes.

TECHNICAL FIELD

The present invention relates to tissue scaffold devices and methods to fabricate tissue scaffold devices.

BACKGROUND

Tendon repair and regeneration into the native nature with biomimicked architecture and function has been an important clinical challenge, which has yet to be solved. It is estimated that damages in tendons are the most common injuries affecting the quality of life, and in the United States alone, over 100,000 surgical repairs are performed annually. However, tendon regeneration into the specialized tissue organization with high mechanical support has been a challenging issue yet to be resolved. Traditional methods including autografting, allografting and xenografting have been developed in a number of tendon repairs with considerable success. Applications of these strategies, however, may meet intrinsic limitations. For example, autografts have limited availability and inevitable damages to the donor site may result in consequent morbidity. Allo-grafts and xeno-grafts are expensive, and they may potentially transmit diseases from the donors to the recipients. Moreover, the failure rates of allo-grafts and xeno-grafts may range from 20% to as high as 90%, for example in chronic rotator cuff repairs, due to factors such as a lack of vascularization as well as poor integration between the grafts and bone. While tissue engineering involving cells and a suitable scaffold could provide the answer to the challenge, none of the presently available tendon scaffolds have shown good efficacy that resembles the natural tendon. Scaffolds like braided fabrics may be dense and therefore limit nutrient transmission and cell infiltration, leading to tissue being formed only on the scaffold surface. Knitted scaffolds may possess internal communicating spaces with good mechanical properties. However, knitted scaffolds may require a gel system such as fibrin and collagen, or a fibrous mesh for cell seeding, adhesion and proliferation. Knitted scaffolds may also lack the capability of reconstructing tendon tissue into the natural anisotropic architecture of tendons. Knitted scaffolds may incorporate anisotropic electrospun mesh to facilitate cell seeding and ordered cell organization. However, the anisotropic electrospun mesh from rotating disk and mandrel may have significant fibrous packing which inhibit cell and tissue ingrowth. Therefore, there is a need for an alternative solution for facilitating tendon repairs.

SUMMARY

According to various embodiments, there may be provided a tissue scaffold device including a porous core including a plurality of fibres; and an outer portion at least substantially surrounding the porous core, the outer portion including a plurality of pores elongated along a longitudinal axis of the tissue scaffold device.

According to various embodiments, there may be provided a method for fabricating a tissue scaffold device, the method including forming a porous core, the porous core including a plurality of fibres; and forming an outer portion at least substantially surrounding the porous core, the outer portion including a plurality of pores elongated along a longitudinal axis of the tissue scaffold device.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DESCRIPTION

Figure 1:
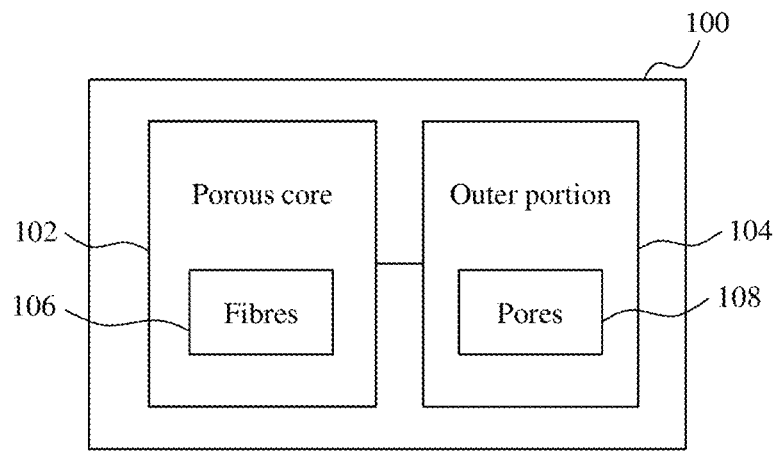
FIG. 1 shows a conceptual diagram of a tissue scaffold device according to various embodiments.

Embodiments described below in context of the devices are analogously valid for the respective methods, and vice versa. Furthermore, it will be understood that the embodiments described below may be combined, for example, a part of one embodiment may be combined with a part of another embodiment.

In order that the invention may be readily understood and put into practical effect, particular embodiments will now be described by way of examples and not limitations, and with reference to the figures.

Various embodiments are provided for devices, and various embodiments are provided for methods. It will be understood that basic properties of the devices also hold for the methods and vice versa. Therefore, for sake of brevity, duplicate description of such properties may be omitted.

It will be understood that any property described herein for a specific device may also hold for any device described herein. It will be understood that any property described herein for a specific method may also hold for any method described herein. Furthermore, it will be understood that for any device or method described herein, not necessarily all the components or steps described must be enclosed in the device or method, but only some (but not all) components or steps may be enclosed.

It should be appreciated and understood that the term "substantially" may include "exactly" and "similar" which is to an extent that it may be perceived as being "exact". For illustration purposes only and not as a limiting example, the term "substantially" may be quantified as a variance of +/−5% from the exact or actual.

In the context of various embodiments, "tissue scaffold device" may be but is not limited to being interchangeably referred to as a "tendon scaffold" or a "tubular scaffold".

In the context of various embodiments, "fibres" may be but is not limited to being interchangeably referred to as "fibers", "filaments" or "fibrillae".

In the context of various embodiments, "pores" may be but is not limited to being interchangeably referred to as "perforative holes", "through-holes" or "elongated pores".

In the context of various embodiments, "outer portion" may be but is not limited to being interchangeably referred to as "shell" or "outer layer".

In the context of various embodiments, "porous core" may be but is not limited to being interchangeably referred to as "core portion" or "inner portion".

Tendon repair and regeneration into the native nature with biomimicked architecture and function has been an important clinical challenge, which has yet to be solved. It is estimated that damages in tendons are the most common injuries affecting the quality of life, and in the United States alone, over 100,000 surgical repairs are performed annually. However, tendon regeneration into the specialized tissue organization with high mechanical support has been a challenging issue yet to be resolved. Traditional methods including autografting, allografting and xenografting have been developed in a number of tendon repairs with considerable success. Applications of these strategies, however, may meet intrinsic limitations. For example, autografts have limited availability and inevitable damages to the donor site may result in consequent morbidity. Allo-grafts and xeno-grafts are expensive, and they may potentially transmit diseases from the donors to the recipients. Moreover, the failure rates of allo-grafts and xeno-grafts may range from 20% to as high as 90%, for example in chronic rotator cuff repairs, due to factors such as a lack of vascularization as well as poor integration between the grafts and bone. While tissue engineering involving cells and a suitable scaffold could provide the answer to the challenge, none of the presently available tendon scaffolds have shown good efficacy that resembles the natural tendon. Scaffolds like braided fabrics may be dense and therefore limit nutrient transmission and cell infiltration, leading to tissue being formed only on the scaffold surface. Knitted scaffolds may possess internal communicating spaces with good mechanical properties. However, knitted scaffolds may require a gel system such as fibrin and collagen, or a fibrous mesh for cell seeding, adhesion and proliferation. Knitted scaffolds may also lack the capability of reconstructing tendon tissue into the natural anisotropic architecture of tendons. Knitted scaffolds may incorporate anisotropic electrospun mesh to facilitate cell seeding and ordered cell organization. However, the anisotropic electrospun mesh from rotating disk and mandrel may have significant fibrous packing which inhibit cell and tissue ingrowth.

FIG. 1 shows a tissue scaffold device 100 according to various embodiments. The tissue scaffold device 100 may include a porous core 102 which may include a plurality of fibres 106; and an outer portion 104 which may at least substantially surround the porous core 102. The outer portion 104 may include a plurality of pores 108 which may be elongated along a longitudinal axis of the tissue scaffold device 100.

In other words, according to various embodiments, a tissue scaffold device 100 may include a porous core 102 and an outer portion 104. The porous core 102 may include a plurality of fibres 106. The outer portion 104 may surround the porous core 102. The outer portion 104 may include a plurality of elongated pores 108. The pores 108 may be elongated along a longitudinal axis, or in other words, along a length of the tissue scaffold device 100. The tissue scaffold device 100 may be at least substantially tubular in shape, or in other words, cylindrical in shape. At least one of the porous core 102 or the outer portion 104 may include at least one of a biopolymer or a biopolymer composite. The porous core 102 may include functionally graded hydroxyapatite. The plurality of fibres 106, which may include electrospun fibres, may be arranged along the longitudinal axis of the tissue scaffold device 100. The plurality of fibres 106 may be aligned on a substrate and the substrate may be rolled up to form a helix. The helix may have a spiral cross-section. The plurality of fibres 106 may be arranged to define a helical channel within the porous core 102. The substrate may be a water soluble film and may include at least one of poly (ethylene oxide) or poly(ethylene glycol). The porous core 102 may be multi-lamellar in structure. The outer portion 104 may include a polymer. Each pore 108 of the plurality of pores 108 of the outer portion 104 may be defined at least substantially entirely though a thickness of the outer portion 104. In other words, each pore 108 may puncture through the outer portion 104. The outer portion 104 may include at least one of a single layer of biopolymer or a single layer of biopolymer composite. The outer portion 104 may include at least one of a bioresponsive material or a bioresorbable material. The outer portion 104 may have at least one of a ridge aligned along the longitudinal axis or a groove aligned along the longitudinal axis. The groove may be sandwiched in between two ridges.

Figure 2:
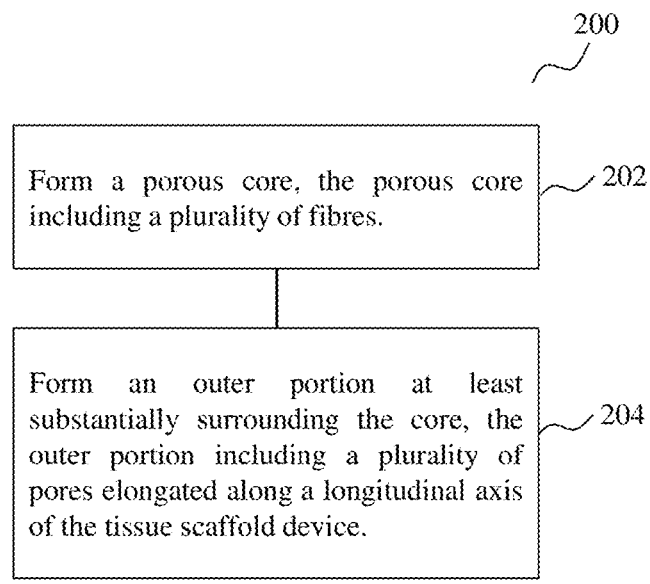
FIG. 2 shows a flow diagram of a method for fabricating a tissue scaffold device, according to various embodiments.

FIG. 2 shows a flow diagram 200 showing a method for fabricating a tissue scaffold device, according to various embodiments. In 202, a porous core may be formed, the porous core including a plurality of fibres. In 204, an outer portion may be formed, the outer portion at least substantially surrounding the porous core, the outer portion including a plurality of pores elongated along a longitudinal axis of the tissue scaffold device.

In other words, according to various embodiments, a method for fabricating a tissue scaffold device may include 202, in which a porous core may be formed; and 204, in which an outer portion may be formed. The porous core may include a plurality of fibres. The outer portion may include a plurality of elongated pores and may at least substantially surround the porous core. The plurality of elongated pores may be elongated along a length of the tissue scaffold device.

The tissue scaffold device and the porous core may each be at least substantially tubular. The process of forming the porous core may include electrospinning the plurality of fibres, and may further include arranging the plurality of fibres along the longitudinal axis of the tissue scaffold device. The process of forming the porous core may also include uniaxially stretching the plurality of fibres and may further include aligning the plurality of fibres on a substrate. The substrate may be a film, which may be water soluble. The process of forming the porous core may further include rolling the substrate along a direction perpendicular to a length of the plurality of fibres, to form a helix structure. The substrate may be formed from at least one of poly(ethylene oxide) or poly(ethylene glycol). The process of forming the porous core may further include arranging the plurality of fibres to form a multi-lamellar porous core. The plurality of fibres may be arranged to define a helical channel within the porous core. The porous core may be formed from at least one of a biopolymer or a biopolymer composite. The porous core may be formed from functionally graded hydroxyapatite. The process of forming the outer portion may include forming a plurality of pores in a sheet which may be at least one of a bioresponsive material or a bioresorbable material. The sheet may be formed from a polymer. Each pore of the plurality of pores may be formed entirely through a thickness of the sheet. The plurality of pores may be formed by laser punching the sheet. The outer portion may be formed by rolling the sheet into a tube and the process of rolling the sheet may include heat welding the sheet. The process of forming the outer portion may include uniaxially stretching the tube along the longitudinal axis, thereby forming at least one of a ridge or a groove on the outer portion. The ridge or the groove may be aligned along the longitudinal axis. The process of forming the outer portion may further include fitting the porous core into the outer portion and relaxing the porous core within the outer portion. The outer portion may be formed from at least one of a biopolymer or a biopolymer composite. The porous core may be formed from at least one of a single layer biopolymer or a single layer biopolymer composite.

Three-dimensional (3D) tissue scaffold devices may be used to aid the tissue engineering of tendon grafts. The tissue scaffold devices may bio-mimic the nature of tendon tissue. The tissue scaffold devices may be capable of triggering native tendon regeneration at the site of tendon repair. The tissue scaffold devices may also provide mechanical support for the tendon growth. A tissue scaffold device, according to various embodiments, may be tubular in shape, for example, including concentric circles or ellipses. The tissue scaffold device may be composed of multi-layered anisotropic geometries. The anisotropic geometries may be provided by at least one of ridges, grooves or fibrillae. The tissue scaffold device may also include interconnected porous channels that are bio-mimical of tendon architecture, while still providing sufficient bending, tensile and torsional strength in order to be resistant to fractures. The anisotropic geometries may be configured to guide organization of tendon cells and secretion of extra-cellular matrix into an aligned architecture. The interconnected porous channels may facilitate transportation of mass with cellular in-growth, to form tendon tissue in 3D. The interconnected porous channels may also establish connection between the reconstructed tendon and its surrounding tissues through integration of other cells and micro vessels.

A tissue scaffold device, according to various embodiments, may be made up of two portions, namely an inner portion and an outer portion. The inner portion may be a multi-lamellar porous portion which has a plurality of fibrillae orientated towards the tubular long axis. The inner portion may provide sites for the growth of inner cells and the tenogenesis of the cells into an ordered 3D tissue architecture. The outer portion may be a single-layered porous portion wrapped around the inner portion. The outer portion may have highly orientated arrays of ridges or grooves arranged along the tubular long axis, in other words, along a longitudinal axis of the tissue scaffold device, or in other words, along a length of the tissue scaffold device. The arrays of ridges or grooves may provide preliminary sites for seeded cell adhesion, alignment and tenogenesis. The outer portion may also include perforative hole structures to allow mass transportation and cell migration across the outer layer, so as to reach the inner portion. The outer portion may also serve as the primary structure for providing at least one of bending, tensile and torsional strength.

A method for fabricating a tissue scaffold device, according to various embodiments, may include fabricating an inner portion of the tissue scaffold device and an outer portion of the tissue scaffold device separately. The method may include uniaxially stretching films made from biopolymers or biopolymer composites to form anisotropic geometries of ridge/groove or fibrillar structures. The biopolymer or biopolymer composites may include collagen and poly (ε-caprolactone) (PCL), with or without incorporation of hydroxyapatite (HA) nanoparticles. The method may further include filling the inner portion into the outer portion and securing the inner portion to the outer portion tightly by relaxing the inner portion when the inner portion is inside the outer portion. The inner portion may have a multi-lamellar structure. The diameter of the inner portion and the diameter of the outer portion may be decided depending on the implant position and the requirement for mechanical strength.

Fabricating the inner portion may include rolling a film with uniaxially-stretched electrospun fibres or filaments, along a direction perpendicular to the aligned fibres or filaments, to form a multi-lamellar helix structure. The film may be a water-soluble polymeric film, such as poly(ethylene oxide) (PEO) or poly(ethylene glycol) (PEG)). In the multi-lamellar helix structure, adjacent lamellae may be separated by a layer of the film. The diameter of the helix structure may be tunable by controlling the quantity of rolled lamellae.

Fabricating the outer portion may include uniaxially stretching a rolled film using heat fusion and punching perforative holes using direct laser drilling, to form a tubular structure covered with highly orientated ridges and grooves. The perforative holes are also referred herein as pores of the outer portion. The process of stretching the rolled film may be performed at a temperature just below the melting point of the rolled film. The parameters of the ridges and grooves, as well as size of the perforative holes, can be adjusted to control the degree of cellular alignment, cell infiltration and vascularization using different draw ratios, for example draw ratios of 2, 3, 4 and 5.

A tubular scaffold according to various embodiments, may serve to combine the properties of the interconnected porosity and anisotropic geometries for enhanced cell infiltration and tissue ingrowth into the scaffold inside, to form natural tendon architecture with aligned organization of both cells and extracellular matrix (ECM) in a real three-dimension. The outer portion may provide the ridge and groove structures as cues for the seeded cell adhesion and aligned growth on the scaffold surface, and the perforative holes for cellular migration and ingrowth across the outer portion into the scaffold. Meanwhile, the inner portion may provide the interconnected porosity, for example from uniaxial stretching of electrospun mesh, within the lamella and a helix channel among the lamellae to connect the pores for further cell migration into the deeper zone of the scaffold and formation of three-dimensional tendon tissue in the natural anisotropic architecture under the guidance of the orientated filaments. The design of the tubular scaffold may allow the incorporation of different materials for distinct aims, for example using poly(ε-caprolactone) (PCL) for the outer portion to provide the primary mechanical support, and using collagen for the inner portion to give biocompatible functions such as tenogenesis. The inner portion of orientated fibrous mesh may be modified further with functionally graded hydroxyapatite to biomimic the structure and composition of the tendon-to-bone interface. The tubular scaffold may therefore realize the integration of these functions, making it more advanced over existing scaffolds which have imperfect properties and lack the robust capability for tendon regeneration. The tubular scaffolds may be used in regenerative medicine to replace a tendon defect or augment the length of a tendon-related tissue in both the upper and lower extremities of the human body.

A tissue scaffold device according to various embodiments may include an inner portion and an outer portion. The inner portion may include a rolled up bundle of fibres. The fibres may first be arranged on a film before being rolled up. In the rolled up bundle of fibres, an outer layer of fibres may be separated from an inner layer of fibres by the film which may be a water-soluble polymeric film such as PEO or PEG. The film may be dissolved in a phosphate buffered saline or a cell culture medium, so that the bundle of fibres form a helix channel to connect the pores within the outer layer of fibres to the pores within the inner layer of fibres. The diameter of the inner portion of the tissue scaffold device may be dependent on the implant site of the tendon scaffold, and may be tunable by controlling the rolled lamella number. The outer portion may be made from uniaxial stretching of the porous tube obtained using heat fusion of a semi-crystalline polymeric such as a PCL film wrapped around a rod with different diameters, for example 1 to 20 mm at a constant draw ratio, for example draw ratio of 4 for PCL film, and temperature just below the melting point, for example 54° C. for PCL film.

A tubular scaffold, according to various embodiments, may have a structure of interconnected porosity, designed to allow mass transportation and cellular ingrowth into inner sites of the tubular scaffold, for forming an ordered tendon architecture in 3D. A method for manufacturing the tubular scaffold may include laser punching and electrospinning. The tubular scaffold may be made up of a first portion and a second portion. The first portion may include an inner multi-lamellar porous portion with fibrillae orientated towards the tubular long axis that would provide sites for inner cell growth and tenogenesis into the ordered tendon architecture in a real three dimension. The second portion may be an outer single-layered porous portion with orientated ridge or groove arrays arranged along the tubular long axis. The orientated ridge or groove arrays may provide preliminary sites for the seeded cell adhesion, alignment, elongation and tenogenesis. The second portion may include perforative hole structures that would allow mass transportation with cell migration across the second portion into the first portion.

Figure 3A:
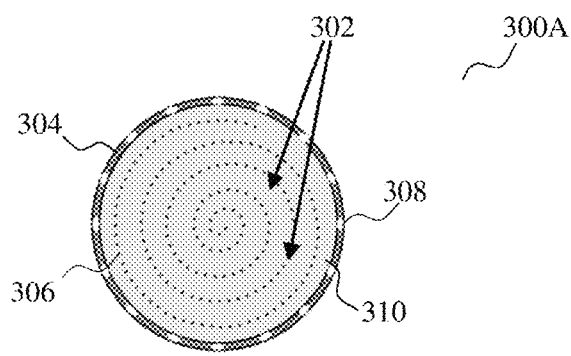
FIGS. 3A-3B show various views of a partially completed tissue scaffold device according to various embodiments.

FIG. 3A shows a top cross-sectional view 300A of a partially-fabricated tubular tendon scaffold, according to various embodiments. The tubular tendon scaffold 300A may include an inner portion 302 and an outer portion 304 surrounding the inner portion 302. The inner portion 302 may include a plurality of fibres 306 adhered to an interlayer 310. The interlayer 310 may include a water-soluble material. The interlayer 310 may be rolled such that the top cross-sectional view 300A shows the interlayer 310 as a spiral. The interlayer 310 may be a water-soluble substrate. The outer portion 304 may be formed from a film that is rolled into a cylindrical structure. The film may have a plurality of elongated holes perforated through a thickness of the film so that the outer portion has a plurality of pores 308 formed therein.

Figure 3B:
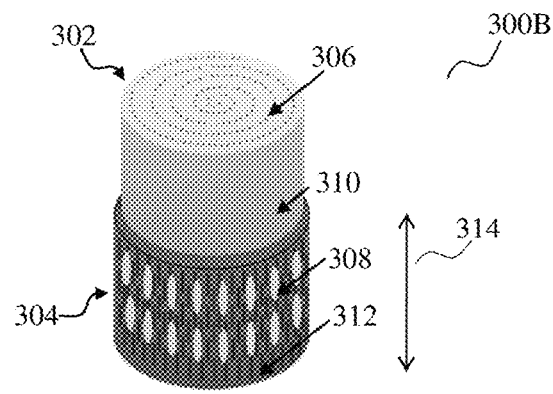

FIG. 3B shows a top-side perspective view 300B of the partially-fabricated tubular tendon scaffold of FIG. 3A. The top-side perspective view 300B shows an external surface of the outer portion 304. The outer portion 304 may have a plurality of pores 308 which are elongated along a longitudinal axis 314 of the tubular tendon scaffold. The external surface of the outer portion may include a plurality of ridges 312 formed therein. The external surface of the outer portion may also include a plurality of grooves formed therein, the grooves being concave spaces between every two ridges 312.

Figure 3C:
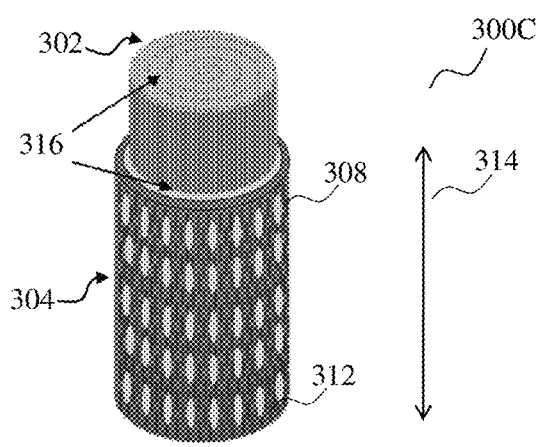
FIG. 3C shows a perspective view of a tissue scaffold device according to various embodiments.

FIG. 3C shows a top-side perspective view 300C of the tubular tendon scaffold of FIG. 3B, after the interlayer 310 has been removed. After the interlayer 310 has been removed, a helix channel 316 may be formed in the inner portion 302. The interlayer 310 may be removed by dissolving the interlayer in water. As shown in 300C, the tubular tendon scaffold can have a 3D anisotropic architecture and interconnected porosity, which makes it suitable for applications in tendon tissue engineering. The anisotropic architecture may be formed by the pores 308 which are elongated along the longitudinal axis 314 and the ridges 312 arranged parallel to the longitudinal axis 314. The anisotropic architecture can provide primary sites for tendon cell adhesion and proliferation, and most importantly, to trigger cellular alignment, elongation and differentiation with secretion of extra-cellular matrix into the ordered organization to generate excellent axial tensile load-bearing capacity.

Figure 4A:
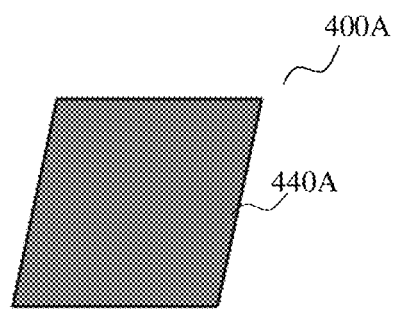
FIGS. 4A-4D show various steps in fabricating an outer portion of a tissue scaffold device according to various embodiments.

FIG. 4A-4D show schematic diagrams illustrating a method for fabricating an outer portion of a tissue scaffold device, according to various embodiments. FIG. 4A shows a diagram 400A showing a film 440A being heat-pressed. The film 440A may be a polymeric film and it may be bioresorbable. The film 440A may be a bioresorbable polymeric film, for example poly(ε-caprolactone) (PCL).

Figure 4B:
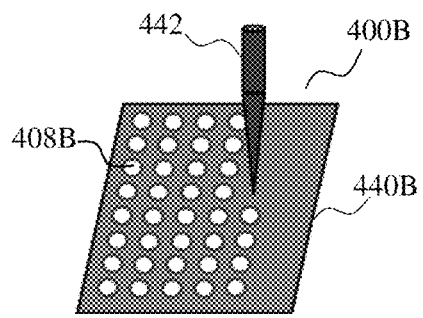

FIG. 4B shows a diagram 400B showing the heat-pressed film 440A of FIG. 4A, being perforated using a laser punch 442 to form a porous film 440B. The heat-pressed film 440A may be laser punched so that a plurality of holes 408B are formed in the film 440A. The holes 408B can be through holes. The laser used for punching the film 440A may be for example, a carbon dioxide continuous wavelength laser at $Energy_{pulse}=0.154$ μJ and $Number_{pulse}=150$, where $Energy_{pulse}$ denotes the energy per pulse or in other words pulse energy, while $Number_{pulse}$ denotes the number of pulses.

Figure 4C:
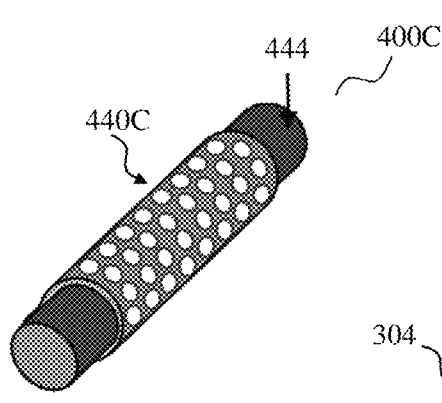

FIG. 4C shows a diagram 400C showing the laser punched film 440B of FIG. 4B, rolled into a tube 440C. The laser punched film 440B may be heated and rolled around a cylinder 444. The rolled laser punched film 440B may be heat welded so that it forms a tube 440C.

Figure 4D:
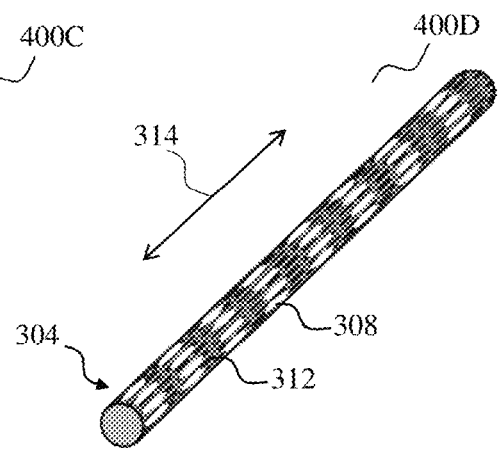

FIG. 4D shows a diagram 400D showing the tube 440C of FIG. 4C, stretched to form an outer portion 304 of a tissue scaffold device. The outer portion 304 of FIG. 4D can be the outer portion 304 of FIGS. 3A-3C and can also be the outer portion 104 of FIG. 1. The tube 440C may be stretched uniaxially along a longitudinal axis 314 so that the plurality of holes 408B are elongated to become pores 308. The plurality of pores 308 may be identical to the pores 308 of FIGS. 3A-3C and the pores 108 of FIG. 1. The stretching of the tube 440C may also result in a plurality of ridges 312 and a plurality of grooves formed on the outer portion 304. The ridges 312 may be micro-ridges and the grooves may be micro-grooves. The tube 440C may be stretched at a constant draw ratio and at a temperature just below the melting point of the film 440A used to make the tube 440C. If the film 440A is PCL, the draw ratio may be 4 and the temperature may be 54° C.

Figure 5A:
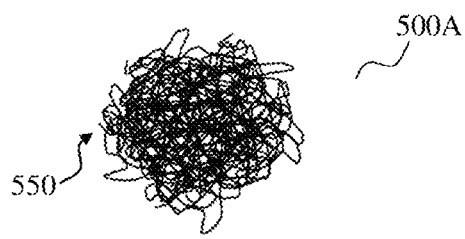
FIGS. 5A-5D show various steps in fabricating an inner portion of a tissue scaffold device according to various embodiments.

FIGS. 5A-5D show schematic diagrams illustrating a method for fabricating an inner portion of a tissue scaffold device, according to various embodiments. The inner portion may be the porous core 102 of FIG. 1. FIG. 5A shows a diagram 500A showing a plurality of fibres 550A which may be polymeric mesh, for example PCL or collagen. The plurality of fibres 550A may be electrospun at room temperature.

Figure 5B:
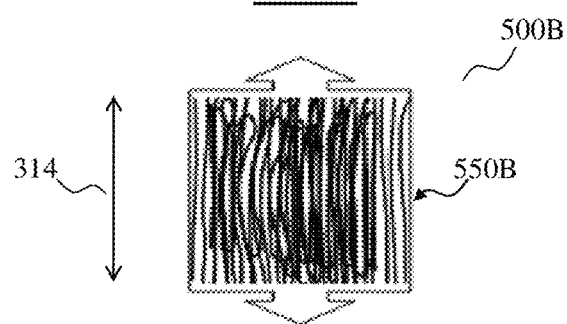

FIG. 5B shows a diagram 500B showing the plurality of fibres 550A of FIG. 5A, stretched to become aligned fibres 550B. The plurality of fibres 550A may be stretched uniaxially along a longitudinal axis 314, with different draw ratios, for example 3 to 5 for PCL mesh, to obtain aligned fibres 550B.

Figure 5C:
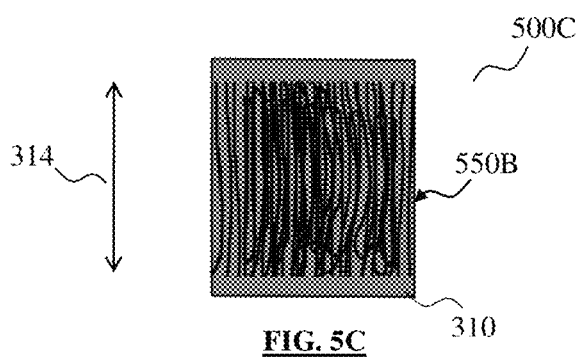

FIG. 5C shows a diagram 500C showing the aligned fibres 550B of FIG. 5B, arranged on an interlayer 310. The interlayer 310 may be a water-soluble film. The aligned fibres 550B may be arranged at least substantially parallel to the longitudinal axis 314.

Figure 5D:
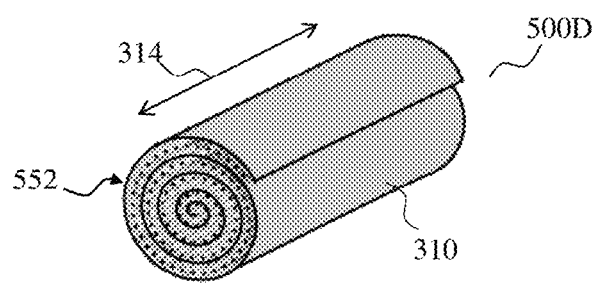

FIG. 5D shows a diagram 500D showing the interlayer 310 together with the aligned fibres 550B, rolled into a spiral or helix structure 552. The interlayer 310 may be rolled in a direction perpendicular to the direction in which the aligned fibres are stretched, in other words, the interlayer 310 may be rolled in a direction perpendicular to the longitudinal axis 314.

The helix structure 552 may then be inserted into the outer portion 304 of FIG. 4D. The helix structure 552 may be expanded while it is inside the outer portion 304, so that the helix structure 552 may be securely coupled to the outer portion 304. The interlayer 310 may be removed subsequently, by for example, dissolving the interlayer 310 in water or in a solution, leaving behind the aligned fibres 550B which have become a helical arrangement, inside the outer portion 304. The helical arrangement of aligned fibres may be the porous core 102 of FIG. 1 and may also be the inner portion 302 of FIG. 3C.

Figure 6A:
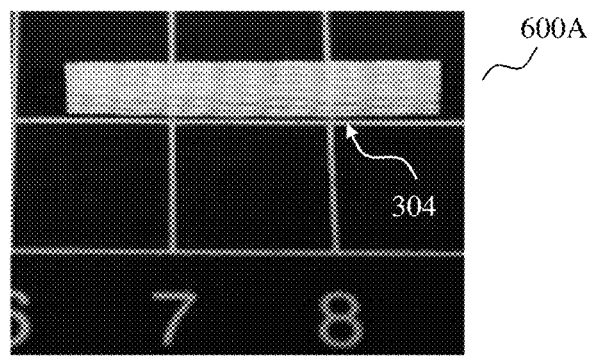
FIG. 6A shows a photograph of an outer portion of a tissue scaffold device according to various embodiments.
Figure 6B:
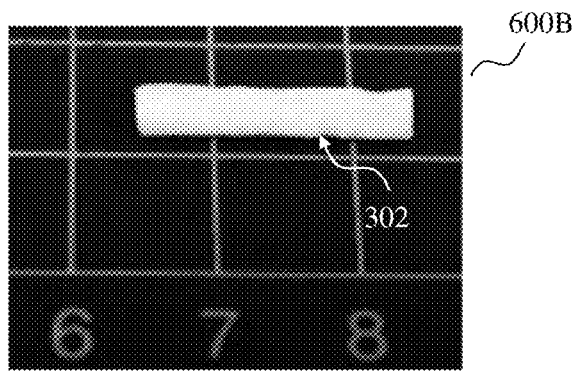
FIG. 6B shows a photograph of an inner portion of a tissue scaffold device according to various embodiments.
Figure 6C:
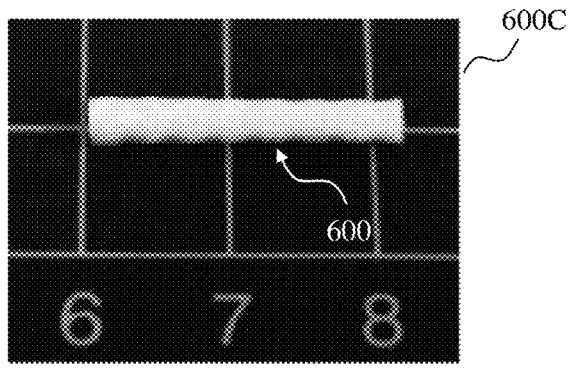
FIG. 6C shows a photograph of a tissue scaffold device according to various embodiments.

FIGS. 6A-6C show photographs of a tissue scaffold device, according to various embodiments. FIG. 6A shows an outer portion 304. The outer portion 304 may serve as the primary structure of the tissue scaffold device to provide bending, tensile and torsional strength.

FIG. 6B shows an inner portion 302. The inner portion 302 may have been fabricated separately from the outer portion 304.

FIG. 6C shows the outer portion 304 and the inner portion 302 combined to form the tissue scaffold device 600. The tissue scaffold device 600 may be identical to the tissue scaffold device 100 of FIG. 1. The tissue scaffold device 600 may have a diameter of between 1 mm to 15 mm.

Figure 7A:
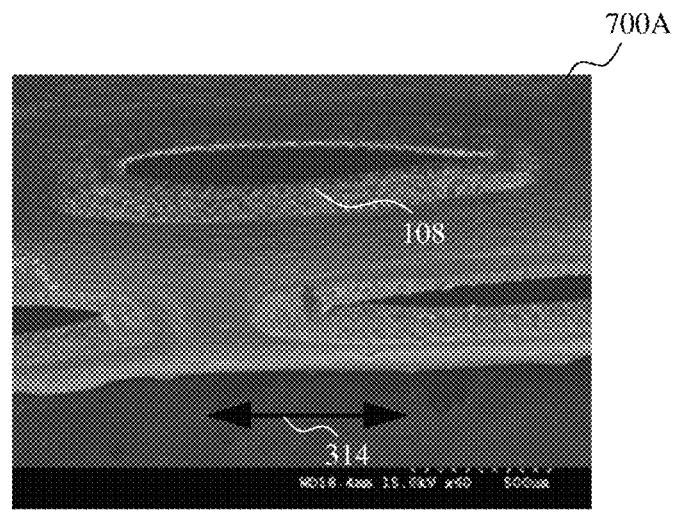
FIGS. 7A-7B show scanning electron microscopy (SEM) images of an outer portion of a tissue scaffold device according to various embodiments.
Figure 7B:
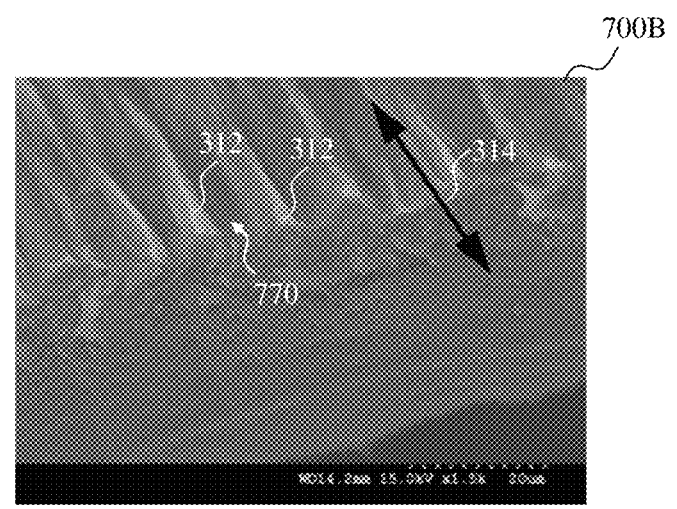

FIGS. 7A-7B show scanning electron microscope (SEM) images of an outer portion of a tissue scaffold device, according to various embodiments. FIG. 7A shows a SEM image 700A showing the perforative holes, in other words, pores 108 on the outer portion of the tissue scaffold device. The pores 108 are elongated along the longitudinal axis 314 of the tissue scaffold device. In other words, the pores 108 may be ellipsoidal in shape and may be longer in the longitudinal axis 314 than in the latitudinal axis which is perpendicular to the longitudinal axis 314. The pores 108 may have been formed by first using direct laser punching on a film to create perforated holes in the film, then stretching the film to transforming the perforated holes into elongated pores 108 which are enlarged in size. The pores 108 may be, for example, at least substantially in the range of 0.5-3 mm in the longitudinal axis 314 and at least substantially in the range of 50-300 μm in the latitudinal axis. The pores 108 may be at least substantially equal to 1 mm in the longitudinal axis and at least substantially equal to 100 μm in the latitudinal axis.

FIG. 7B shows a SEM image 700B showing the outer portion of the tissue scaffold device of FIG. 7A. The outer portion has a plurality of ridges 312 and a plurality of grooves 770. There is a groove 770 in between every two ridges 312. As can be seen from FIG. 7B, the ridges 312 and the grooves 770 are parallel to the longitudinal axis 314. The ridges 312 and the grooves 770 can be formed, through uniaxial stretching. The ridges 312 may be at least substantially in the range of 30-90 μm in length and the distance between adjacent ridges 312 may be at least substantially in the range of 6-17 μm while the depth of the ridges 312 may be at least substantially equal to 700 nm. The ridges 312 may be orientated towards the stretching direction along the longitudinal axis 314, on both the inner and outer surfaces of the inner portion. The diameter of the outer portion is dependent on the size of the inner portion to be inserted, and can be achieved, for example 1-15 mm by uniaxial stretching of the polymeric tubes at different diameters, for example 1-20 mm.

Figure 8A:
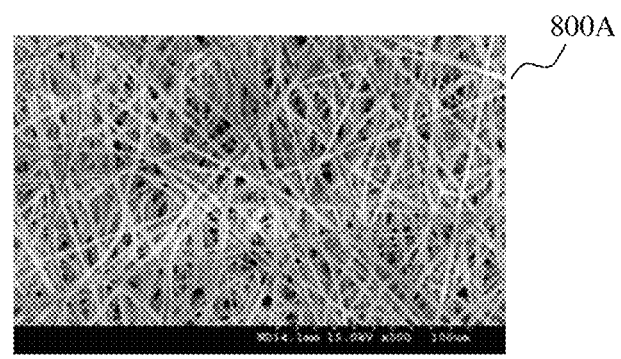
FIGS. 8A-8C show SEM images of fibres.
Figure 8B:
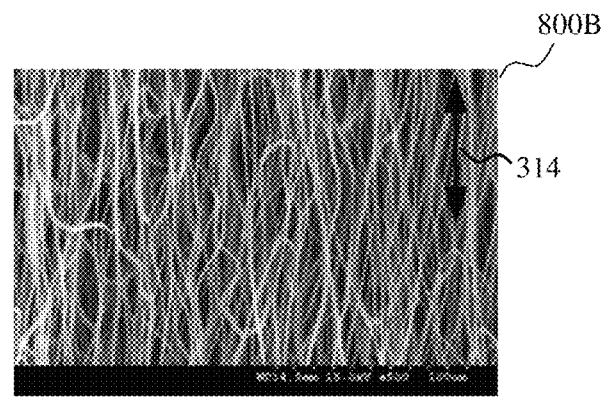
Figure 8C:
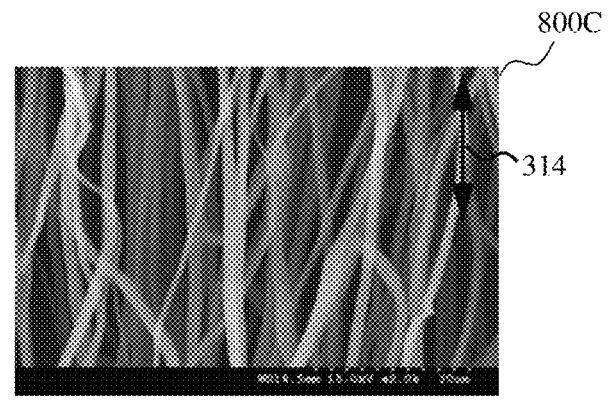

FIGS. 8A-8C show SEM images of fibres for using in an inner portion of a tissue scaffold device according to various embodiments, at different stages of fabrication of the inner portion.

FIG. 8A shows a SEM image 800A showing random electrospun mesh. As shown in 800A, the electrospun fibres are random in their orientation.

FIG. 8B shows a SEM image 800B showing uniaxially-stretched electrospun mesh. The random electrospun mesh of FIG. 8A may be stretched along a longitudinal axis 314 so that the previously randomly-orientated fibres or filaments become orientated to be at least substantially parallel to the longitudinal axis 314.

FIG. 8C shows a magnified image 800C of the SEM image 800B of FIG. 8B. The magnified image 800C shows the uniaxially-stretched mesh. The filaments of the uniaxially-stretched mesh are orientated along the stretching direction parallel to the longitudinal axis 314. The filaments are wavy-like and form interconnected porosity in between the filaments.

Figure 9:
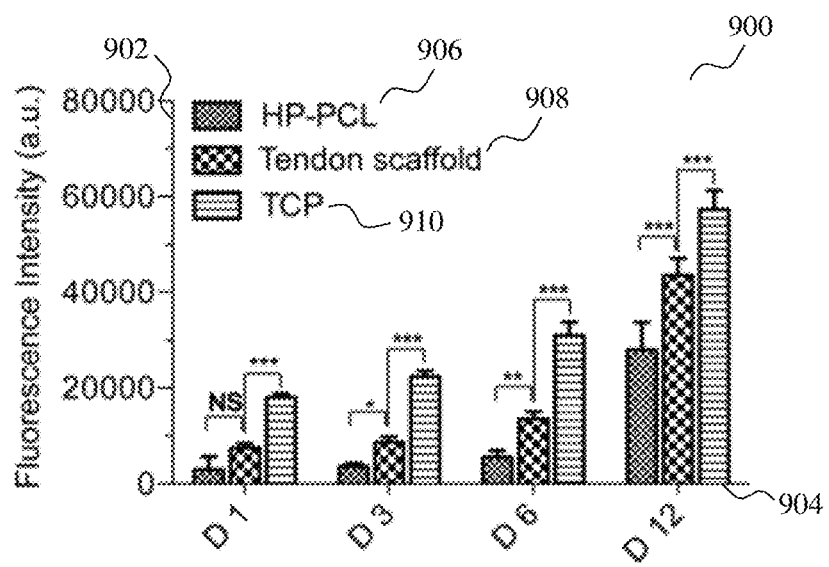
FIG. 9 shows a graph showing bar charts of fluorescence intensity taken at various time durations of culturing tenocytes.

FIG. 9 shows a graph 900 showing the cytocompatibility of the tendon scaffold, in other words the compatibility of tenocytes with the tendon scaffold. An experiment was conducted to investigate the potential of a tissue-engineered tendon scaffold according to various embodiments, for clinical translation. Graph 900 shows a comparison of the growth of tenocytes on the tendon scaffold, as compared to the growth of tenocytes on heat-pressed PCL (HP-PCL) and the growth of tenocytes on a tissue culture plate (TCP). A first sample of human tenocytes was seeded onto HP-PCL to serve as a negative control; a second sample of human tenocytes was seeded onto the tendon scaffold; and a third sample of human tenocytes was placed on the TCP to serve as a positive control. Each of the first sample, second sample and the third sample contained human tenocytes with densities of 10,000 per $cm^2$. Each of the first sample, the second sample and the third sample were cultured for 12 days. Using an alamar blue assay, the proliferation of tenocytes is presented as fluorescence intensity. The sample size is 6. The graph 900 includes a vertical axis 902 and a horizontal axis 904. The vertical axis 902 indicates fluorescence intensity expressed in arbitrary units (a.u.) while the horizontal axis 904 indicates the number of days for which samples of human tenocytes were cultured. In other words, the vertical axis 902 also represents the amount of tenocytes. The graph 900 also includes bar charts 906, 908 and 910. Bar charts 906 represent the fluorescence intensity of the first sample; bar chart 908 represents the fluorescence intensity of the second sample; and bar chart 910 represents the fluorescence intensity of the third sample. Each of the bar charts 906, 908 and 910 are charted for culture durations of 1 day (D1), 3 days (D3), 6 days (D6) and 12 days (D12). The p-values, also denoted as p, were computed for each of the fluorescence intensities obtained for each sample, so as to ascertain if there was any statistical difference between the compared two sample groups. The bar charts are denoted with "*" where $p<0.05$; "" where $p<0.01$; "*" where $p<0.001$ and "NS" where no significant difference was observed. The p-value gives the probability of getting the results as obtained in the experiment, given that the null hypothesis is true. For example: when $p<0.05$ in a test, it means that more than 95% of the results of one sample group were assumed to be different from those of the other sample group. "0.95", "0.99" and "0.999" are the threshold values often chosen for performing p-value analysis, which represent three significance levels ("0.05", "0.01" and "0.001", respectively) of the test. In the graph 900, the results are obtained from a statistical analysis. As shown in the graph 900, the tendon scaffold supported the continuous proliferation of human tenocytes over the investigating period of 12 days. Compared to the HP-PCL, tenocytes cultured on the tendon scaffold proliferated at an enhanced rate, approaching to that of the TCP, with increased culture time.

Figure 10:
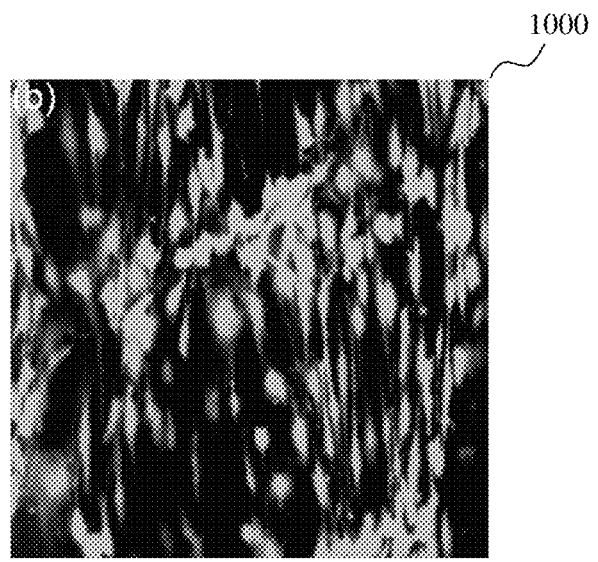
FIG. 10 shows a photograph showing live tenocytes.

FIG. 10 shows a photograph 1000 showing human tenocytes on the tendon scaffold after 13 days of culture. The tenocytes were stained using a Fluorescein Diacetate/Propidium Iodide (FDA/PI) assay so that live cells would appear to be green while dead cells would appear to be red. The green-colored portions of the original photo appear as light grey in the photograph 1000 which is a grayscale version of the original photo. No red colour is observed in the original photo. As such, photograph 1000 shows that the tendon scaffold allowed non-cytotoxic growth of the human tenocytes, with approximately 100% of the tenocytes surviving after 13 days of culture.

Figure 11:
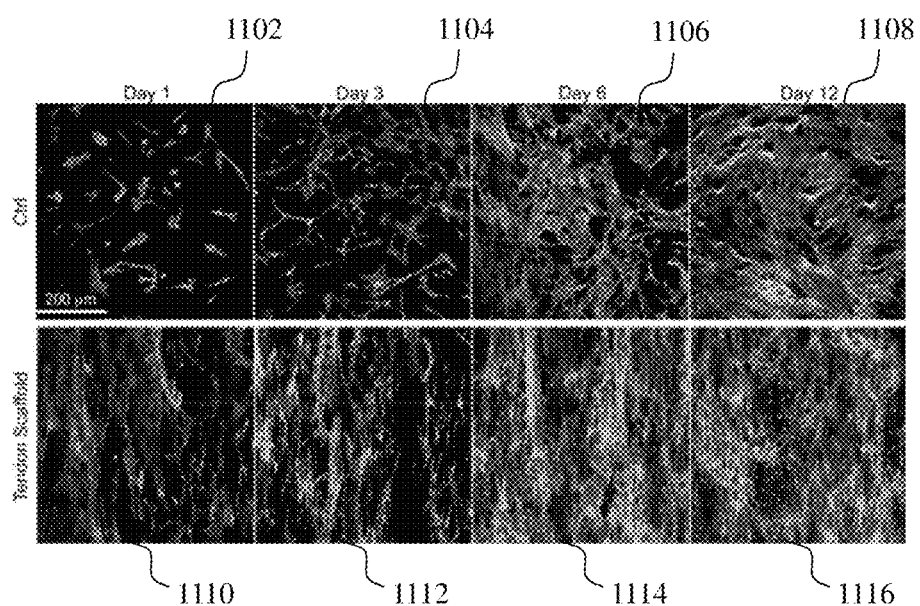
FIG. 11 shows various photographs of cell architectures.

FIG. 11 shows photographs 1102-1116 showing cell architectures of human tenocytes. Human tenocytes of 10,000 per $cm^2$ density were seeded onto the tendon scaffold, as well as on HP-PCL which served as a negative control. The human tenocytes were cultured for a plurality of time durations and labeled using cytoskeleton F-actin and nucleus DNA staining. Photographs 1102, 1104, 1106 and 1108 show the cell architecture of tenocytes on HP-PCL, after durations of 1 day, 3 days, 6 days and 12 days respectively. Photographs 1110, 1112, 1114 and 1116 show the cell architecture of tenocytes seeded onto the tendon scaffold, after durations of 1 day, 3 days, 6 days and 12 days respectively. A comparison of the photographs shows that the tissue-engineered tendon scaffold has demonstrated capability of guiding cell architectural regeneration as in native tendons. The tenocytes exhibited aligned growth with orientated F-actin filaments guided by the engineered tendon scaffold in photographs 1110, 1112, 1114 and 1116. The native tendon-like cell architecture was fast established for the tenocytes even after just 1 day of culturing. Furthermore, the orientation of cells which form the native tendon-like cell architecture remained consistent over 12 days. In contrast, human tenocytes cultured on HP-PCL remained randomly organized even when the cells reached confluence. Therefore, the tendon scaffold has demonstrated its capability to aid reconstruction of tendon cellular architecture.

Figure 12A:
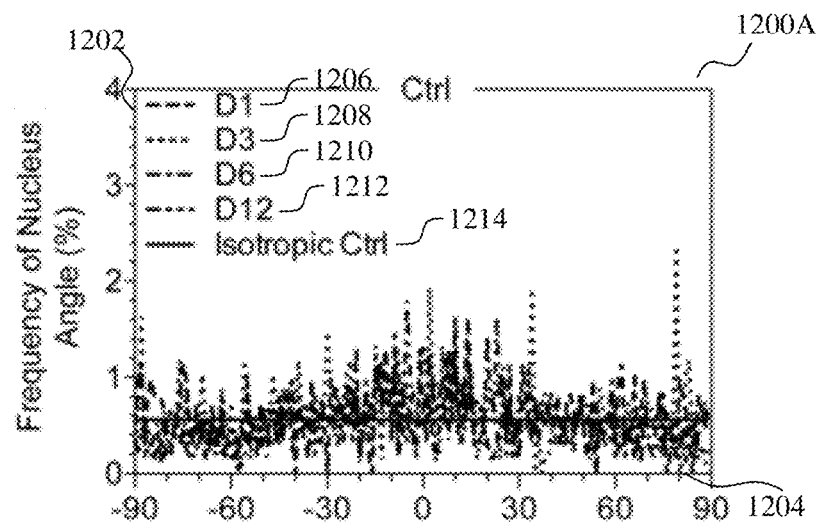
FIG. 12A shows a graph showing an angular distribution of cell nuclei in a control sample.

FIG. 12A shows a graph 1200A showing a distribution of nucleus angles of tenocytes in a control sample. The graph 1200A includes a vertical axis 1202 and a horizontal axis 1204. The vertical axis 1202 indicates frequency expressed in percentage (%) while the horizontal axis 1204 indicates nucleus angle expressed in degrees (°). The graph 1200A also includes a first plot 1206 showing the distribution of nucleus angles after 1 day of culturing, a second plot 1208 showing distribution of nucleus angles after 3 days of culturing, a third plot 1210 showing distribution of nucleus angles after 6 days of culturing, a fourth plot 1212 showing distribution of nucleus angles after 12 days of culturing and a fifth plot 1214 showing an isotropic control sample.

Figure 12B:
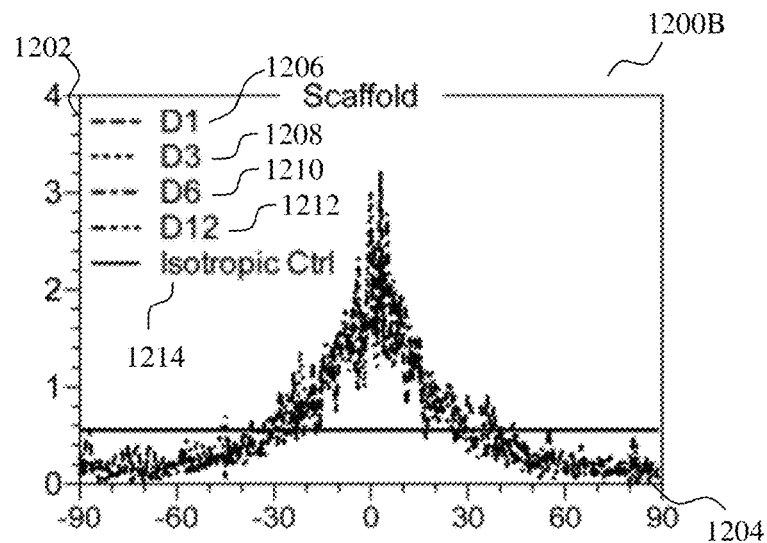
FIG. 12B shows a graph showing an angular distribution of cell nuclei for tenocytes seeded on a tissue scaffold device.

FIG. 12B shows a graph 1200B showing a distribution of nucleus angles of tenocytes which are seeded onto a tendon scaffold. The graph 1200B includes a vertical axis 1202 and a horizontal axis 1204. The vertical axis 1202 indicates frequency expressed in percentage (%) while the horizontal axis 1204 indicates nucleus angle expressed in degrees (°). The graph 1200B also includes a first plot 1206 showing the distribution of nucleus angles after 1 day of culturing, a second plot 1208 showing distribution of nucleus angles after 3 days of culturing, a third plot 1210 showing distribution of nucleus angles after 6 days of culturing, a fourth plot 1212 showing distribution of nucleus angles after 12 days of culturing and a fifth plot 1214 showing an isotropic control sample. As can be seen from the graphs 1200A and 1200B, the tendon-scaffold-resulted cell architecture of tenocytes was coupled with a concentrated angle distribution of cellular nuclei of within ±30° over 12 days of culturing, while the nucleus angles exhibited more even distribution for control groups.

Figure 13A:
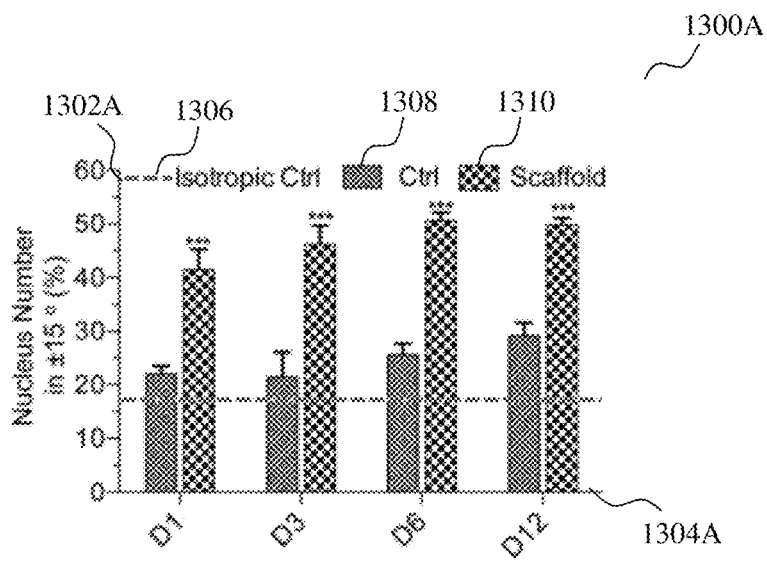
FIG. 13A shows a graph showing numbers of nuclei within an angle of ±15° for various time durations of culturing tenocytes.

FIG. 13A shows a graph 1300A showing cell alignment efficiency of tenocytes, presented as the number of cell nuclei in angles of ±15° as compared to an isotropic control. The isotropic control is an even distribution of cell nuclei with an efficiency of ~16.7%.The graph 1300A includes a vertical axis 1302A and a horizontal axis 1304B. The vertical axis 1302A indicates nucleus number within angle of ±15° as expressed in percentage (%) while the horizontal axis 1304A indicates time duration of culture. The graph 1300A further includes a first chart 1306 representing an isotropic control sample; a second chart 1308 representing a control sample, for example, tenocytes seeded on HP-PCL; and a third chart 1310 representing tenocytes seeded on a tendon scaffold. The sample size is 4. The bar charts are denoted with "*" where $p<0.001$ as compared to the negative control 1308. Quantitative analysis showed that human tenocytes cultured on the tendon scaffold, as represented by the third chart 1310 obtained significant increase in the number of cell nuclei in ±15°, as compared to 1.7-2.1x, $p<0.001$ for the control sample represented by the second chart 1308**, suggesting a higher cell alignment efficiency achieved.

Figure 13B:
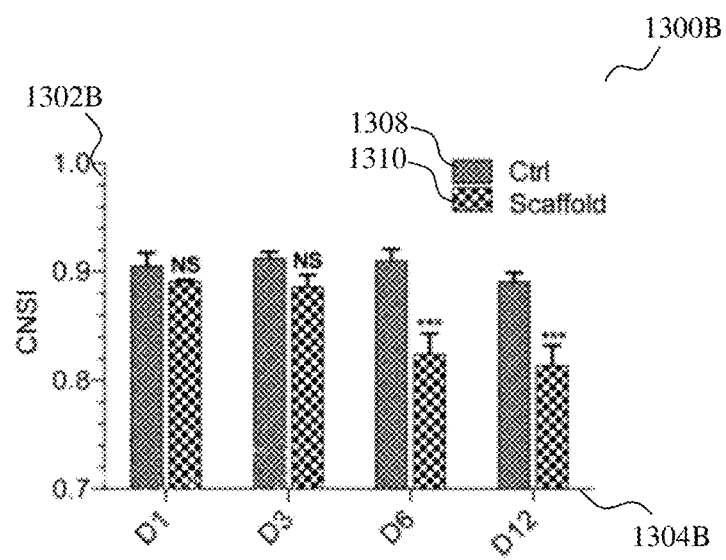
FIG. 13B shows a graph showing cell nucleus shape index (CNSI) for various time durations of culturing tenocytes.

FIG. 13B shows a graph 1300B showing cellular elongation of tenocytes over time. The graph 1300B includes a vertical axis 1302B indicating the cell nucleus shape index (CNSI) and a horizontal axis 1304B indicating time duration of culture. The graph 1300B also includes a first chart 1308 representing a control sample and a second chart 1310 representing tenocytes seeded onto a tendon scaffold. The sample size is 4. The bar charts are denoted with "*" where $p<0.001$ and with "NS" where there is no significant difference as compared to the negative control 1308. As can be seen from the graph 1300**B, a higher elongation of cell nuclei was observed for the human tenocytes after 6 days of culturing on the tendon scaffold as compared to the tenocytes in the control sample, indicating that genetic changes occurred. The CNSI of the tenocytes on the tendon scaffold was about 0.9 times that of the CNSI of the tenocytes in the control sample, with $p<0.001$. These observations demonstrated that the tendon scaffold engineered were able to deliver regulation on cellular nuclei of tendon cells, and thus would facilitate reconstruction of tendon cell architecture from the genetic to morphological levels.

In the following, a pre-clinical trial to demonstrate the applicability of a tissue scaffold device for in-vivo tendon reconstruction will be described. A pre-clinical large animal model of tendon defects can be established using a micro-pig (μ-pig), with a tissue-gap created in the patellar tendons of two hind-legs. A tissue scaffold device according to various embodiments can be sterilized using γ-irradiation before being implanted into the micro-pig to fill the tissue-gap. The tissue scaffold device can retain its porous and anisotropic structure even after the sterilization.

Figure 14A:
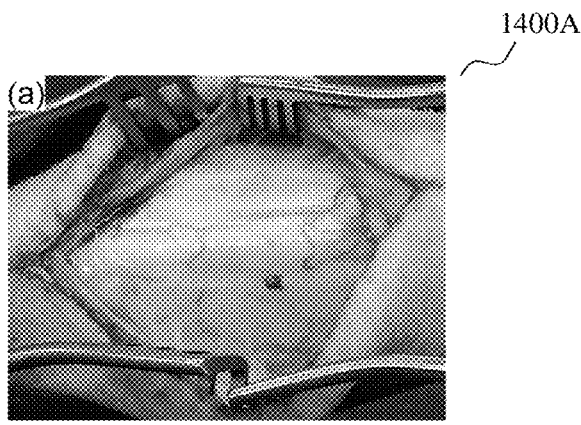
FIG. 14A shows a photograph showing a hind-leg patellar tendon in a pre-clinical model.

FIG. 14A shows a photograph 1400A showing a hind-leg patellar tendon in the pre-clinical model.

Figure 14B:
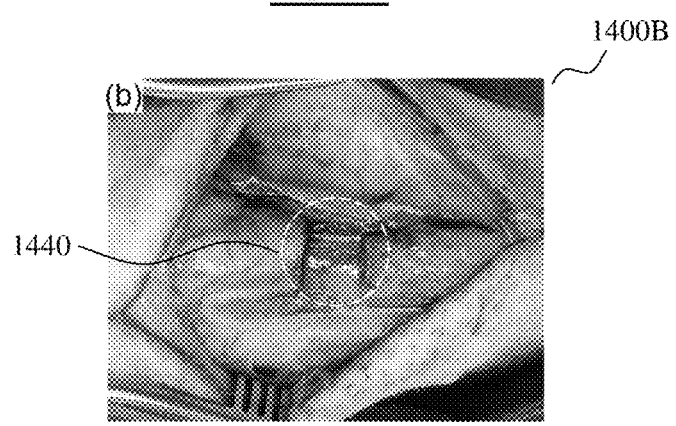
FIG. 14B shows a photograph showing a tendon defect created in the hind-leg patellar tendon of FIG. 14A.

FIG. 14B shows a photograph 1400B showing a tendon defect 1440 created in the hind-leg patellar tendon. The tendon defect 1440 has a tissue-gap of about 10 mm in length.

Figure 14C:
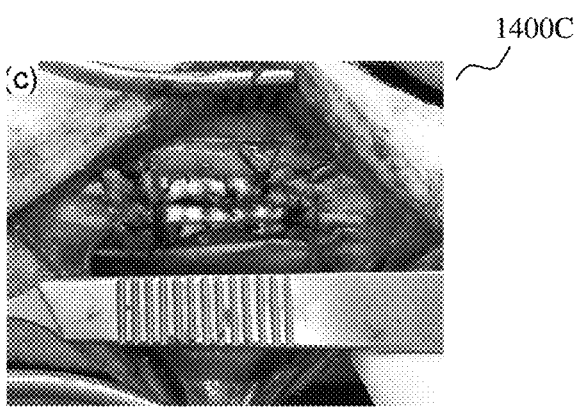
FIG. 14C shows a photograph showing a tissue scaffold device according to various embodiments, implanted in the pre-clinical model.

FIG. 14C shows a photograph 1400C showing a tissue scaffold device implanted to connect two ends of the native patellar tendon. The tissue scaffold device underwent μ-irradiation for sterilization, and retained its intact porous and anisotropic structures. The tissue scaffold device can fill the tissue defect 1440 by connecting the two ends of the tissue gap in the tendon. The tissue scaffold device exhibited operative suturability with ease of handling, and allowed for the post-operative hind-legs to stretch and bend.

Figure 15A:
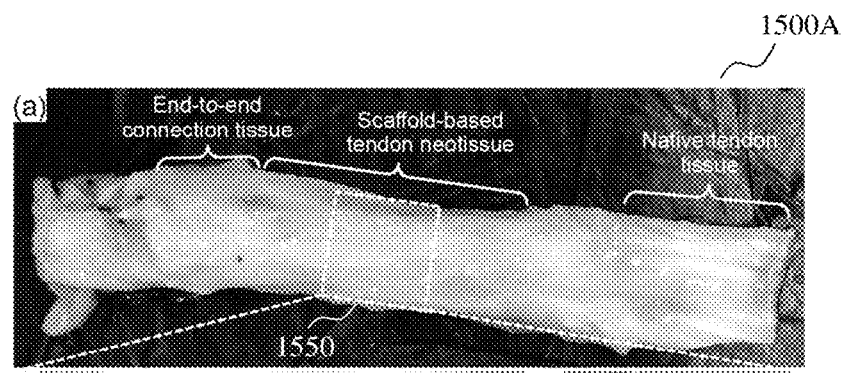
FIG. 15A shows a photograph showing the in-vivo tendon regeneration in the pre-clinical model.

FIG. 15A shows a photograph 1500A showing the in-vivo tendon regeneration in the pre-clinical large animal model of FIGS. 14A-14C. The photograph 1500A shows micro-pig patellar tendon collected 6 weeks after the tissue scaffold was implanted to repair the tissue defect. As can be seen in the photograph 1500A, a tendon neotissue 1550 was formed. The tendon defect was successfully repaired with the tendon neotissue 1550 not only in the regions at the two ends of the tissue scaffold device, but also over the length of the tissue scaffold device. The tendon neotissue 1550 has also been shown to integrate well with the native tendon tissues.

Figure 15B:
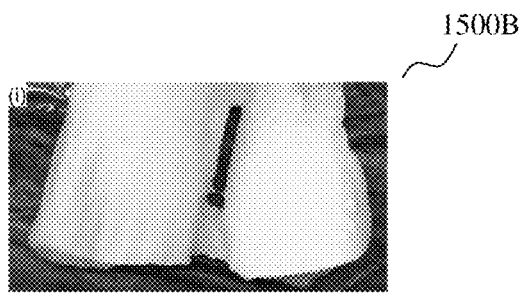
FIG. 15B shows a photograph showing a magnified view of a tendon neotissue.

FIG. 15B shows a photograph 1500B showing a magnified view of the tendon neotissue 1550. It can be seen from the photograph 1500B, that the tendon neotissue 1550 exhibited a normal glistening white appearance similar to that of the native tendon.

Figure 15C:
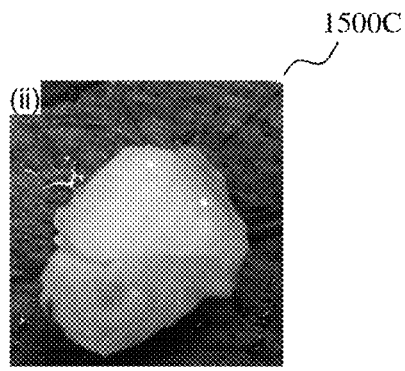
FIG. 15C shows a photograph showing a cross-section of the tendon neotissue.

FIG. 15C shows a photograph 1500C showing a cross-section of the tendon neotissue 1550. A plurality of portions at different healing phases can be observed from the cross-section of the tendon neotissue 1550. The reconstructed tendon neotissue was then sectioned at various planes along its longitudinal direction, and analyzed using hematoxylin and eosin (H&E) staining to evaluate the potential of the tissue scaffold device in reconstructing tendon histological components, by comparing the histological analysis of the tendon neotissue to the histological analysis of the native micro-pig patellar tendons.

Figure 16:
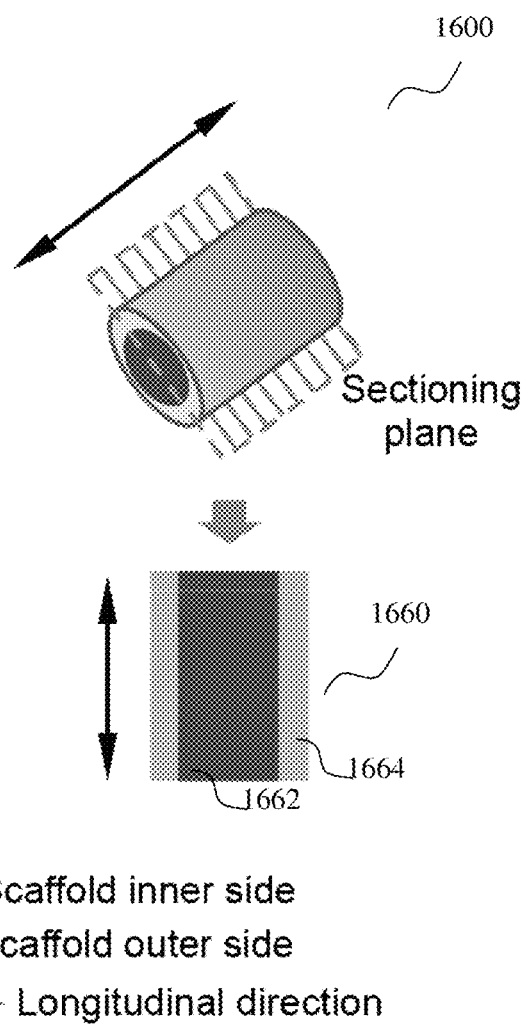
FIG. 16 shows a schematic diagram showing the methodology for sectioning the tendon neotissue.

FIG. 16 shows a schematic diagram showing the methodology for sectioning the reconstructed tendon neotissue. A sample 1660 of the reconstructed tendon neotissue is first obtained by cutting off the two end portions of the reconstructed tendons, along the longitudinal direction. The sample 1660 is then sectioned at various planes parallel to the longitudinal direction. The sample 1660 includes an inner section formed in the inner portion of the scaffold, also referred herein as the scaffold inner side 1662. The sample 1660 also includes an outer section formed at the outer portion of the scaffold, also referred herein as the scaffold outer side 1664.

Figure 17A:
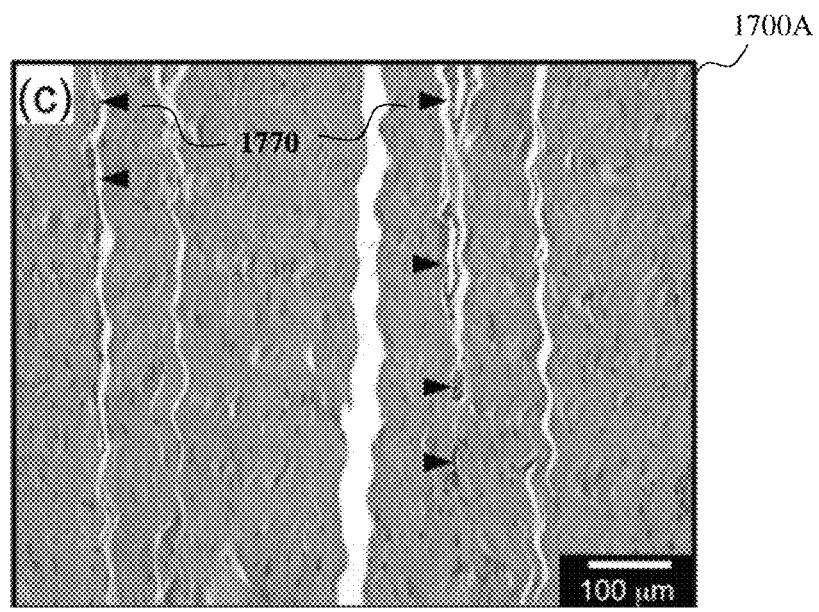
FIG. 17A shows the histological analysis of a native micro-pig patellar tendon.

FIG. 17A shows an image 1700A showing the histological analysis of a native micro-pig patellar tendon using H&E staining. The histological analysis of the native micro-pig patellar tendon is used as a basis of comparison for the histological analysis of the reconstructed tendon neotissue. Blood vessels 1770 are visible in the image 1700A, as annotated by arrows.

Figure 17B:
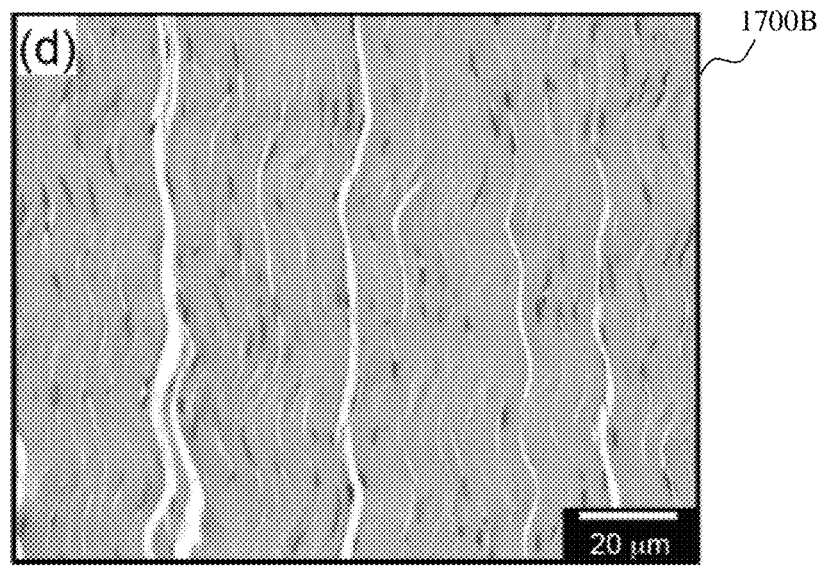
FIG. 17B shows a magnified view of FIG. 17A.

FIG. 17B shows a magnified view 1700B of the image 1700A of FIG. 17A.

Figure 18A:
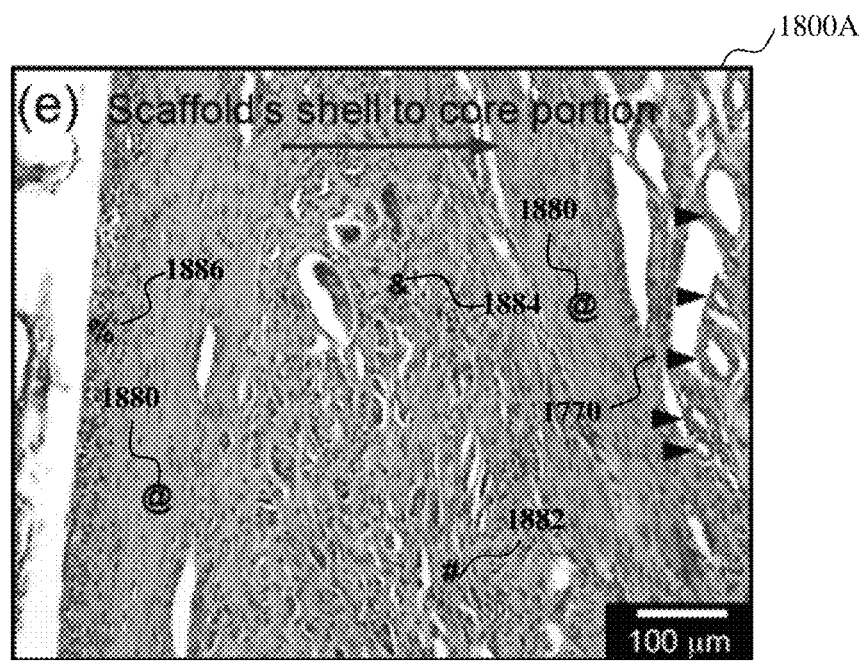
FIG. 18A shows the histological analysis of a reconstructed tendon neotissue within the tissue scaffold device.

FIG. 18A shows an image 1800A showing the histological analysis of a reconstructed tendon neotissue using H&E staining, within the tissue scaffold device. In the image 1800A, blood vessels 1770, inflammation 1886, fibroplasias 1884, tissue remodelling 1882 and neotissue maturation 1880 can be seen. The blood vessels 1770 are indicated in the image with arrows; inflammation is indicated with the symbol "%"; fibroplasias 1884 is indicated with the symbol "&"; tissue remodelling 1882 is indicated with the symbol "#"and neotissue maturation 1880 is indicated with the symbol "@". The H&E staining results showed that cells and vessels can penetrate across the shell (also referred herein as the outer layer) of the tissue scaffold device scaffold, approaching into the deep core portion of the tissue scaffold device. The tissue scaffold device can simultaneously trigger multiple healing responses. As shown in the image 1800A, areas near the shell of the tissue scaffold device are found with inflammation 1886 while areas in the core portion are found with fibroplasias 1884, tissue remodeling 1882 and tissue maturation 1880 after the tissue scaffold device has been implanted for 6 weeks.

Figure 18B:
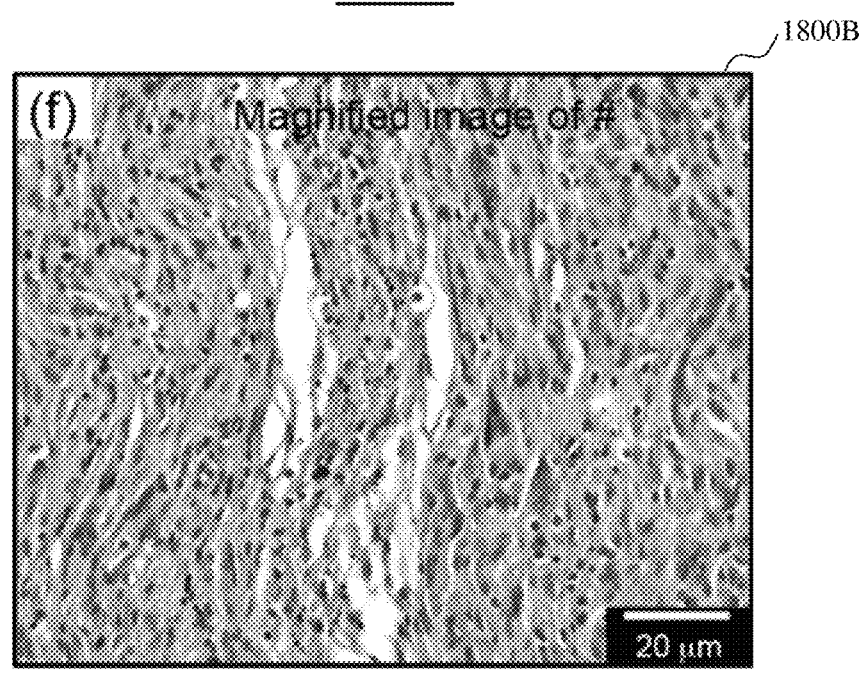
FIG. 18B shows a magnified view of a portion of FIG. 18A where tissue remodeling is visible.

FIG. 18B shows a magnified view 1800B of the portion of the image 1800A where tissue remodelling 1882 is visible. It can be seen from the magnified view 1800B that extracellular matrix (ECM) had begun to be deposited on the core portion of the tissue scaffold device and cells were observed to re-organize into a wave-like aligned pattern along the longitudinal direction of the tissue scaffold device.

Figure 19A:
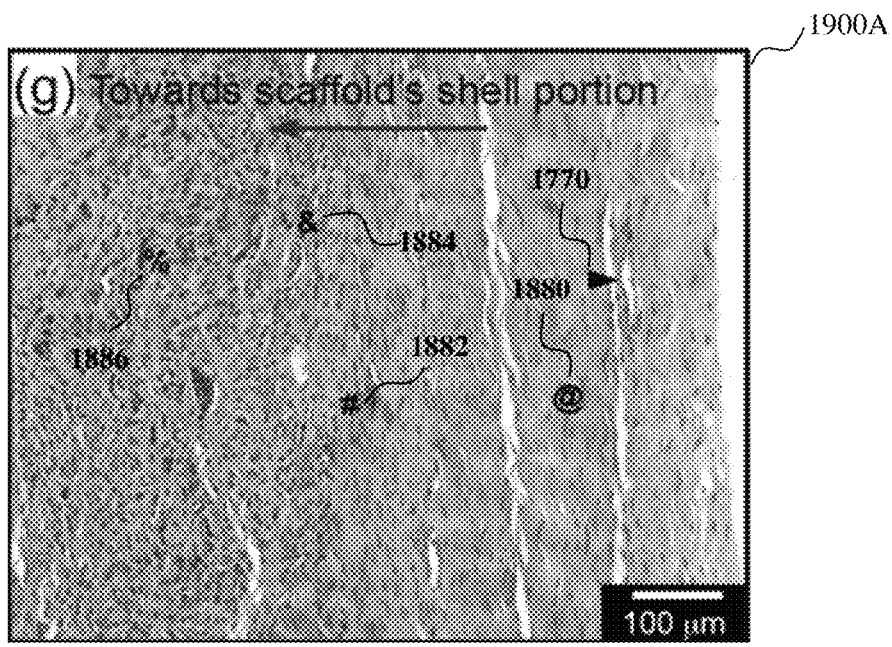
FIG. 19A shows the histological analysis of a reconstructed tendon neotissue at a peripheral region of the tissue scaffold device.

FIG. 19A shows an image 1900A showing the histological analysis of a reconstructed tendon neotissue using H&E staining, at a peripheral region of the tissue scaffold device. Tendon neotissue formation was observed in the peripheral region of the tissue scaffold device, with similar multiple healing responses to those occurring within the tissue scaffold device as shown in FIG. 18A-18B. Comparing the above multiple healing phases, the consolidated mature tendon neotissue at both the inner and outer sides of the tissue scaffold device exhibited a lower cellularity, with an elevated content of collagen deposition, formation of fibril bundles, and wave-like alignment of ECM filaments approaching to those of the native micro-pig patellar tendon as shown in FIG. 17A-B.

Figure 19B:
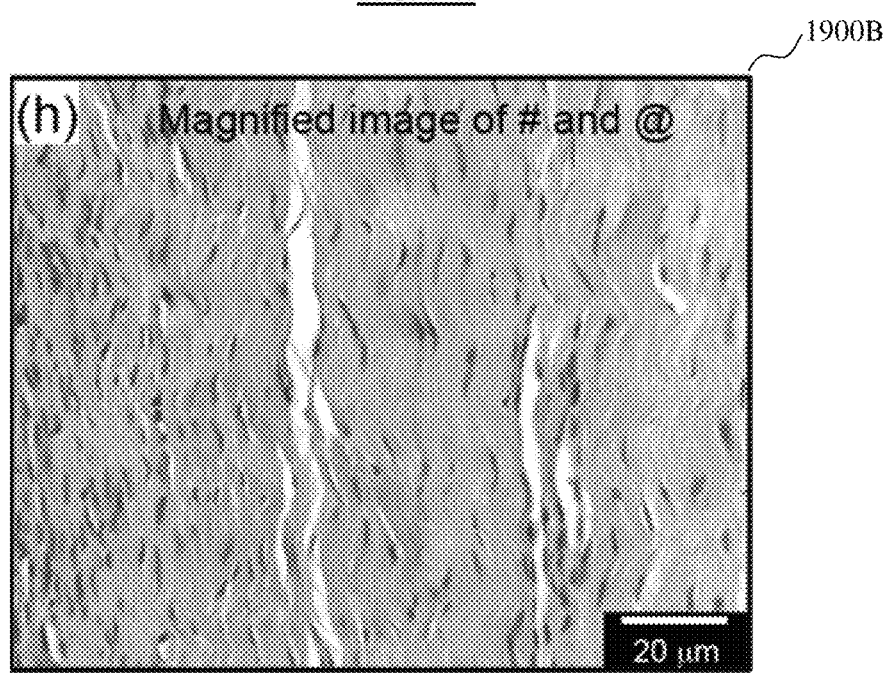
FIG. 19B shows a magnified view of a portion of FIG. 19A where tissue remodeling and tissue maturation is visible.

FIG. 19B shows a magnified view of a portion of FIG. 19A where tissue remodeling and tissue maturation are visible.

While embodiments of the invention have been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced. It will be appreciated that common numerals, used in the relevant drawings, refer to components that serve a similar or the same purpose.

The invention claimed is:

1. A method for fabricating a tissue scaffold device, the method comprising:
    forming a helical-structured core comprising multiple fibrous layers defining a helical channel of the helical-structured core; and
    forming an outer portion at least surrounding the helical-structured core, the outer portion comprising a plurality of pores and ridges elongated along a longitudinal axis of the tissue scaffold device;
    wherein forming the helical-structured core comprises
        aligning a plurality of fibers on a water-soluble substrate;
        rolling the water-soluble substrate along a direction perpendicular to a length of the plurality of fibers to form a helix structure; and
        dissolving the water-soluble substrate to form the helical channel.

2. The method as in claim 1, wherein forming the helical-structured core comprises electrospinning the plurality of fibers for forming the helically-rolled fibrous layer.

3. The method as in claim 1, wherein forming the helical-structured core comprises uniaxially stretching the plurality of fibers.

4. The method as in claim 1, wherein forming the outer portion comprises forming a plurality of pores in the sheet.

5. The method as in claim 4, wherein forming the outer portion further comprises rolling the sheet into a tube.

6. The method as in claim 5, wherein rolling the sheet into the tube comprises heat welding the sheet.

7. The method as in claim 5, wherein forming the outer portion further comprises uniaxially stretching the tube along the longitudinal axis.

8. The method as in claim 1, wherein forming the outer portion comprises fitting the helical-structured core into the outer portion and relaxing the helical-structured core within the outer portion.

\* \* \* \* \*